US011278625B2

(12) United States Patent
Pora et al.

(10) Patent No.: US 11,278,625 B2
(45) Date of Patent: Mar. 22, 2022

(54) FILM-FORMING COMPOSITIONS BASED ON STARCHY MATERIAL AND ARTICLES OBTAINED THEREOF

(71) Applicant: Roquette Freres, Lestrem (FR)

(72) Inventors: Bernard Pora, Shanghai (CN); Yong Miao, Shanghai (CN); Jovin Hasjim, Shanghai (CN)

(73) Assignee: Roquette Freres, Lestrem (FR)

( * ) Notice: Subject to any disclaimer, the term of this patent is extended or adjusted under 35 U.S.C. 154(b) by 0 days.

(21) Appl. No.: 15/750,041

(22) PCT Filed: Aug. 5, 2016

(86) PCT No.: PCT/EP2016/068743
§ 371 (c)(1),
(2) Date: Feb. 2, 2018

(87) PCT Pub. No.: WO2017/021533
PCT Pub. Date: Feb. 9, 2017

(65) Prior Publication Data
US 2018/0221486 A1    Aug. 9, 2018

(30) Foreign Application Priority Data

Aug. 6, 2015 (EP) ..................................... 15306275

(51) Int. Cl.
| *A61K 47/22* | (2006.01) |
| *A61K 9/48* | (2006.01) |
| *A61K 9/00* | (2006.01) |
| *A61K 9/28* | (2006.01) |
| *A61K 9/70* | (2006.01) |
| *A61K 47/26* | (2006.01) |
| *A61K 47/32* | (2006.01) |
| *A61K 47/36* | (2006.01) |
| *C08J 5/18* | (2006.01) |

(52) U.S. Cl.
CPC .............. *A61K 47/22* (2013.01); *A61K 9/006* (2013.01); *A61K 9/0056* (2013.01); *A61K 9/282* (2013.01); *A61K 9/286* (2013.01); *A61K 9/2826* (2013.01); *A61K 9/4816* (2013.01); *A61K 9/70* (2013.01); *A61K 47/26* (2013.01); *A61K 47/32* (2013.01); *A61K 47/36* (2013.01); *C08J 5/18* (2013.01); *C08J 2303/02* (2013.01); *C08J 2405/00* (2013.01); *C08J 2405/04* (2013.01); *C08J 2439/06* (2013.01)

(58) Field of Classification Search
CPC ...... A61K 47/22; A61K 47/26; A61K 9/0056; A61K 9/006; A61K 9/282; A61K 9/2826; A61K 9/286; A61K 9/70; A61K 47/32; A61K 47/36; A61K 9/4816; C08J 5/18; C08J 2439/06; C08J 2303/02; C08J 2405/00; C08J 2405/04
See application file for complete search history.

(56) References Cited

U.S. PATENT DOCUMENTS

| 6,375,981 B1 | 4/2002 | Gilleland et al. |
| 2012/0178858 A1 | 7/2012 | Wnuk et al. |
| 2013/0078289 A1* | 3/2013 | Siepmann .............. A61K 47/36 424/400 |

* cited by examiner

*Primary Examiner* — Quanglong N Truong

(57) ABSTRACT

The instant invention relates to new film-forming compositions based on starchy material, comprising isosorbide. The instant invention also relates to products made from the film-forming compositions of the invention, in particular hard and soft capsules shells, and to methods for the manufacture of such products.

14 Claims, No Drawings

FILM-FORMING COMPOSITIONS BASED ON STARCHY MATERIAL AND ARTICLES OBTAINED THEREOF

CROSS REFERENCE TO RELATED APPLICATIONS

This application is a U.S. national stage application of International patent application No. PCT/EP2016/068743, filed Aug. 5, 2016, which claims the priority of European application No. 15306275.7, filed Aug. 6, 2015, the subject matter of each incorporated in their entirety by reference herein.

FIELD OF THE INVENTION

The instant invention relates to new film-forming compositions based on starchy material, comprising isosorbide. The instant invention also relates to products made from the film-forming compositions of the invention, in particular hard and soft capsules shells, and to methods for the manufacture of such products.

PRIOR ART

Capsules are solid dosage forms with hard or soft shells, classically intended for oral administration. They are of various shapes and sizes and usually contain one or more active ingredient(s) and one or more excipient(s).

Hard capsules have shells consisting of two prefabricated cylindrical sections that fit together. One end of each section is rounded and closed and the other is open. The contents of hard capsules are usually in solid form (powder or granules).

Soft capsules have thicker shells than hard capsules. The shells are of one piece and various shapes. The contents of soft capsules are usually solutions or suspensions of the active ingredient(s) in non-aqueous liquids.

Capsule shells are classically made of gelatin, the consistency of which may be adjusted by the addition of a plasticizer such as glycerol or sorbitol.

Gelatin is a translucent, colorless, brittle (when dry), flavorless material, derived from collagen obtained from various animal by-products, mainly pig skin, bovine skin, and bones.

After dissolution in hot water and cooling, gelatin forms a semi-solid colloidal gel which has many advantages for the preparation of capsules. Gelatin has rapid gelling ability, excellent film forming properties, and ability to impart oxygen impermeability. Films formed from plasticized gelatin set very quickly and have high wet film strength. They are also very elastic with good clarity. Plasticized gelatin also has a relatively low viscosity, even when used at high solids concentrations. In addition, when gelatin is in the presence of water at room temperature, it swells but does not go into solution until heat is applied.

For many years, gelatin had good press. However, following the emergence of bovine spongiform encephalitis, the use of gelatin in edible preparations has become very controversial.

Moreover, the use of gelatin is not compatible with certain beliefs, or religious practices. Some vegetarians and vegans notably refuse to consume any products derived from animals and consequently boycott all edible products containing gelatin. Gelatin also has the disadvantages of batch property variations, limited availability and high cost.

Because of these shortcomings, those industries where the need for gelatin is greatest, have long sought means for getting rid of gelatin, in favor of 100% plant-based solutions.

To this end, various alternatives have been proposed, but these alternatives lacked consistency from the industrial point of view, so that they were never developed further.

Hydroxypropyl methylcellulose (HPMC) or carrageenan for instance, which are vegetarian-acceptable alternatives to gelatin, are way too expensive to produce, even more than gelatin.

Starchy-based formulations have also been employed. However the films formed thereof lack transparency and stability. After several months, the strength, the flexibility and the plasticity of the films obtained thereof decrease. This results in parallel, in an increase of their friability and opacity. Also, for the preparation of capsule shells, the time required for the step of dipping is relatively long with those formulations (20 seconds compared to 1 or 2 seconds for gelatin solution).

Indeed, a useful gelatin replacer should provide properties equivalent to those of the gelatin which it is replacing for a particular application; and this for a reasonable price. For capsules manufacture, the capsules should possess the properties of good wet and dry film strength, suitable solubility parameters, temperature and pressure seal ability, film clarity, film flexibility, edibility, inertness to drugs or other materials to be encapsulated, and rapid setting from a hot liquid to form a gel.

The inventors succeeded in remedying the drawbacks of gelatin-free and starchy-based compositions of prior art, by developing particular film-forming compositions, which notably comprise isosorbide and hydrolyzed alkylated starch.

OBJECTIVES

It was thus an object of the invention to provide film-forming compositions based on starchy material making it possible partial replacement of gelatin in these compositions, ideally total replacement of gelatin in these compositions.

In particular, it was an object of the present invention to provide film-forming compositions suitable for the preparation of articles such as edible capsule shells.

It was another object of the invention to provide film-forming compositions using bio-based materials, preferably excluding material of animal origin, which are easy to manufacture and easy to handle, and which does not involve excessive costs for their preparation and use.

BRIEF DESCRIPTION OF THE INVENTION

Therefore a first aspect of the invention relates to a film-forming composition comprising:
- a hydrolyzed alkylated starch;
- an additional hydrocolloid;
- isosorbide;
- a plasticizer.

According to a second aspect, the invention relates to a product comprising the film-forming composition of the invention, or obtainable from the film-forming composition of the invention.

According to a third aspect, the invention relates to a method for the manufacture of a product, comprising a step of forming a film or a gel from a film-forming composition of the invention.

According to a fourth aspect, the invention relates to the use of isosorbide for partial, or preferably total, replacement of gelatin in a film-forming composition comprising a hydrolyzed alkylated starch, or in a product comprising such film-forming composition or in a product obtainable from such film-forming composition.

DETAILED DESCRIPTION OF THE INVENTION

In the film-forming compositions of the invention, the hydrolyzed alkylated starch likely acts as a film-forming agent, whereas the other hydrocolloid acts as a gelling agent.

As for the isosorbide, it is not clearly understood how it acts in these compositions. In any case, it seems clear that isosorbide positively impacts the plasticizer's effects, meaning that the presence of both isosorbide and plasticizer are of importance in these compositions. This is apparent from Examples 1 and 2.1 hereinafter.

The film-forming compositions of the invention do not require the use of gelatin. Partial and even total replacement of gelatin is thus possible for the preparation of articles such as capsule shells.

The film-forming compositions of the invention can advantageously be entirely composed of natural-origin materials, in particular and advantageously of non-animal origin.

Contrary to the film-forming compositions of prior art, these compositions allow the preparation of articles with great properties, notably with respect to mechanical resistance, solubility, transparency, flexibility, drought resistance, moisture proof and disintegration. Also, these film-forming compositions are easy to use: the capsules manufacturers can replace their classic gelatin compositions by the film-forming compositions of the invention by using the equipment which is already in their possession; and this, without requiring significant changes in the process settings.

The articles manufactured by using the film-forming composition of the invention can comply with important application of the cosmetic, pharmaceutical, food, animal feed and in between industries.

As a result, the film-forming compositions of the invention can be used for many applications like for the preparation of capsule shells, for the preparation of orodispersible films, or for tablet and pellet coating.

Film-Forming Composition

The film-forming compositions of the invention are characterized by the fact that they comprise:
a hydrolyzed alkylated starch;
an additional hydrocolloid;
isosorbide;
a plasticizer.

It is reminded herein that the expression "film-forming composition" classically refers to a composition comprising at least one polymer (film-forming agent), said polymer being able to form an essentially continuous film in the presence of a solvent, water in particular. In the instant invention, film-forming compositions are in particular starchy film-forming compositions, i.e. using a starch, as main film-forming agent.

It is also reminded that the expression "starch" classically refers to the starch isolated from any suitable botanical source, by any technique well known to those skilled in the art. Isolated starch typically contains no more than 3% of impurities; said percentage being expressed in dry weight of impurities with respect to the total dry weight of isolated starch. These impurities typically comprise proteins, colloidal matters and fibrous residues. Suitable botanical source includes for instance legumes, cereals, tubers.

In this regard, the starch useful to the invention is preferably a pea starch, a maize starch, a tapioca starch or a mixture thereof, preferably a pea starch.

Preferably, the hydrolyzed alkylated starch of the invention is derived from a starch exhibiting an amylose content chosen within the range of from 25 to 45%, preferably of from 30 to 45%, preferably of from 35 and 40%; these percentages being expressed in dry weight of amylose with respect to the total dry weight of said starch from which it is derived.

The starch useful to the invention is modified: it is hydrolyzed (or "fluidified") and alkylated, preferably hydroxypropylated.

The hydrolyzed alkylated starch useful to the invention might also have undergone other physical and/or chemical modifications, as long as it does not interfere with the desired properties of said hydrolyzed alkylated starch. An example of chemical modification is cross-linking. Physical modifications preferably comprise gelatinization, and pregelatinization.

The hydrolyzed hydroxypropylated starch useful to the invention generally has a content of hydroxypropyl groups of between 1 and 50%, even of between 1 and 15%, even of between 5 and 9%, for instance of between 6 and 8%; said percentages being expressed in dry weight of hydroxypropyl groups with respect to the total dry weight of hydroxypropylated starch, and determined by Proton nuclear magnetic resonance (proton NMR), for instance according to the standards EN ISO 11543:2002 F.

The hydrolyzed alkylated starch useful to the invention, in particular the hydrolyzed hydroxypropylated starch useful to the invention, preferably has a weight average molecular weight of between 20 and 2 000 kDa, preferably of between 100 and 1 000 kDa, for instance of between 200 and 800 kDa, for instance of between 200 and 500 kDa, or of between 200 and 400 kDa, or of between 200 and 300 kDa; said weight average molecular weight being determined by HPSEC-MALLS (High Performance Size Exclusion Chromatography coupled on-line with Multiple Angle Laser Light Scattering).

Suitable hydroxypropylated hydrolyzed starches are commercially available, for instance those marketed under the brand LYCOAT® (ROQUETTE).

It is also reminded that the expression "hydrocolloid" classically refers to cold-water-soluble macromolecules (soluble in water, at a temperature chosen from 20 to 25° C.) which, in aqueous solution, impede the water mobility and thus influence the rheological behavior of the solution.

The additional hydrocolloid useful to the invention can be selected from polysaccharides, from proteins, for instance gelatin, from synthetic polymers such as hydroxypropylmethylcellulose, hydroxypropylcellulose, polyvinyl alcohol, or from mixtures thereof. It is preferably selected from polysaccharides and/or from proteins.

It is even more preferably selected from carrageenans, alginates, pullullans, glucomannans, for instance Konjac glucomannans, xanthans, tara gums, pectins, arabic gums or mixtures thereof. It is for instance selected from mixtures of carrageenans and alginates, for instance of K-carrageenan and of sodium alginate, preferably in a dry weight ratio of carrageenans to alginates of between 0.1:1 and 1:1, preferably of between 0.2:1 and 0.9:1, preferably of between 0.2:1 and 0.8:1, for instance of between 0.2:1 and 0.5:1, even of between 0.2:1 and 0.4:1.

Of course, if gelatin is used, it preferably represents no more than 50% of the film-forming composition, preferably no more than 30%, preferably no more than 10%, preferably no more than 5%, preferably no more than 1%; these percentages being expressed in dry weight of gelatin with respect to the dry weight of the total film-forming composition. Even more preferably, the film-forming composition of the invention is free of gelatin.

Preferably, in the film-forming compositions of the invention, the dry weight ratio of additional hydrocolloid to hydrolyzed alkylated starch is of between 0.01:1 and 0.50:1, preferably of between 0.03:1 and 0.30:1, preferably of between 0.04:1 and 0.10:1, for instance of between 0.05:1 and 0.09:1.

The plasticizer useful to the invention can for instance be selected from sorbitol, glycerol, trehalose, polyethylene glycol, triethyl cictrate, polysorbate, Carnauba wax, hydrogenated castor oil, or from mixtures thereof. It is preferably selected from glycerol, threhalose, sorbitol, or from mixtures thereof.

Preferably, the plasticizer useful to the invention at least comprises sorbitol, or a mixture of glycerol and sorbitol. In the latter case, the sorbitol or the mixture of sorbitol and glycerol preferably represents more than 50% of the plasticizer, preferably more than 80%, preferably more than 90%; these percentages being expressed in dry weight of sorbitol or in dry weight of sorbitol and glycerol with respect to the dry weight of whole plasticizer. More preferably, the sorbitol or the mixture of sorbitol and glycerol is the only plasticizer of the film-forming composition.

Preferably, in the film-forming compositions of the invention, the dry weight ratio of the sum of isosorbide and plasticizer to hydrolyzed alkylated starch is of between 0.05:1 and 0.80:1, preferably of between 0.05:1 and 0.70:1, preferably of between 0.05:1 and 0.60:1, for instance of between 0.10:1 and 0.50:1.

In particular, for the preparation of hard capsule shells, this dry weight ratio of the sum of isosorbide and plasticizer to hydrolyzed alkylated starch is preferably of between 0.05:1 and 0.50:1, preferably of between 0.10:1 and 0.40:1, even more preferably of between 0.20:1 and 0.30:1.

For the preparation of soft capsule shells, this dry weight ratio of isosorbide and plasticizer to hydrolyzed alkylated starch is preferably of between 0.20:1 and 0.70:1, preferably of between 0.30:1 and 0.60:1, for instance of between 0.40:1 and 0.50:1.

Preferably, in the film-forming compositions of the invention, the dry weight ratio of plasticizer to isosorbide is of between 0.01:1 and 10:1, preferably of between 0.02:1 and 8:1, preferably of between 0.03:1 and 5:1, for instance of between 0.04:1 and 4:1.

In a particular preferred embodiment of the invention, the film-forming compositions of the invention are composed of:
- 50 to 90% of a hydrolyzed alkylated starch, preferably 55 to 80%;
- 1 to 10% of an additional hydrocolloid, preferably 2 to 8%, for instance 3 to 7%;
- 0.5 to 30% of isosorbide, preferably 1 to 30%, for instance 5 to 25%;
- 0.5 to 30% of a plasticizer, preferably 0.5 to 25%;
- optionally 0 to 0.50% of a buffering agent, for instance KCl, preferably 0.01 to 0.50%, preferably 0.05 to 0.20, for instance 0.10 to 0.15%;
- optionally 0 to 10% of other ingredients, preferably 0 to 5%, typically 0 to 3% or even 0 to 1%;

said percentages being expressed in dry weight of ingredient with respect to the total dry weight of said film-forming composition, and their sum being equal to 100%.

The film-forming compositions of the invention can indeed comprise other ingredients, as long as it does not interfere with the desired properties of said film-forming compositions. Such other ingredients can be for instance: surface-active substances, opaque fillers, conservatives, antimicrobial agents, sweeteners, flavouring substances, colors, brightening agents, disintegrating agents, glidants, lubricants, substances capable of modifying the disintegration behavior of the film in the gastrointestinal tract.

Preferably, the film-forming compositions of the invention are essentially composed of, or even entirely composed of natural-origin ingredients, preferably of non-animal origin, preferably of plant-origin.

Preferably, the film-forming compositions of the invention are composed of edible ingredients.

Preferably, the film-forming compositions of the invention are capable of forming a film which is soluble in water at a temperature chosen from 4 to 50° C., even from 20 to 40° C., for instance at room temperature (chosen from 20 to 25° C.), or at 37.5° C.

To be able to form a film, the ingredients of the film-forming composition must be dissolved in suitable solvent, just prior to its use. This can be achieved by simply mixing the ingredients with a solvent, under heating if necessary, for instance at about 90° C.

Accordingly, the film-forming composition of the invention can be in the liquid form, in particular in the form of a solution, preferably in the aqueous form.

In general, this liquid film-forming composition has a dry matter content by weight of between 10 and 70%, even of between 20 and 60%, even of between 20 and 50%, even of between 25 and 45%, for instance of between 30 and 45%.

Film-forming compositions in the powdery form are also covered in the instant invention. These typically are "ready-to-use" powdery compositions. In the latter case, the use of the powdery composition classically only requires the addition of a solvent, preferably water, and solubilization of said powdery composition in said solvent.

In the case where the film-forming composition is in the powdery form, it can be prepared by simply mixing the various powdery ingredients composing it. However it can advantageously be in the form of a spray-dried powder. In the latter case, the film-forming composition is advantageously prepared first by dissolving the ingredients in any suitable solvent, preferably water. The liquid composition thus obtained is then spray-dried so as to obtain a powder. This spray-dried form has the advantage of being very easy to use, for instance by the capsules manufacturers: dissolution of this powder is easier to achieve, at lower temperatures, as compared to simple physical mixtures.

Articles and Methods for Their Preparation

The film-forming compositions of the invention are capable of forming edible water-soluble films or gels, more or less rigid, which are useful for the manufacture of many products. These products typically are those classically using gelatin in their preparation. These products preferably are edible products. They can be of food, of pharmaceutical, of cosmetic and/or of nutraceutical interest. They can be for humans or for animals.

The instant invention thus also relates products comprising the film-forming composition of the invention, or obtainable from the film-forming composition of the invention, as well as to methods for the manufacture of such products, said methods comprising a step of forming a film or a gel from a film-forming composition of the invention.

In a first and preferred embodiment of the invention, the products are capsule shells, including hard and soft capsule shells, or films.

The term "film" as defined herein, refers to a thin and flat product, having a substantially planar surface, a thickness ranging from 5 to 3000 μm, preferably of between 20 and 200 μm, more preferably of between 50 and 90 μm, and whose thickness is relatively small compared to its length and its width. It is preferably orodispersible films, but may also include films for any other application in which obtaining a film of such a thickness is advantageous, for example films with carrier such as patches for transdermal administration of an active principle by applying the patch on the skin, topical cosmetic or pharmaceutical films to put on the skin, or films to be dissolved, for example in cosmetics, food, or drinks.

The invention thus more specifically covers a capsule shell or a film comprising:
a hydrolyzed alkylated starch;
an additional hydrocolloid;
isosorbide;
a plasticizer.

Preferably, the composition of the dry matter of the capsule shell or film is like described before, for the film-forming composition according to the invention.

In the case of hard capsule shells, the solid content of the product is preferably higher than 80%, even higher than 85%, usually of between 85 and 95%. In the case of soft capsule shells, the solid content is preferably higher than 40%, even higher than 45%, usually of between 50 and 90%, for instance of between 50 and 60%. In the case of films, the solid content is usually of between 50 and 90%.

Preferably, the capsule shells and films of the invention are soluble in water at a temperature chosen from 4 to 50° C., even from 20 to 40° C., for instance at room temperature (chosen from 20 to 25° C.), or at 37.5° C.

Preferably, the capsule shells and films of the invention are edible.

The instant invention of course also covers capsules including such capsule shells.

The films and capsule shells of the invention can be obtained more precisely according to a method comprising the steps of:
(a) providing a film-forming composition according to the invention in the liquid form;
(b) molding the articles with the composition obtained in step (a);
(c) drying the molded composition obtained in step (b);
(d) recovering the article thus obtained.

For the manufacture of hard capsule shells, the step (b) is in particular performed by dipping pins into the film-forming composition.

For the manufacture of soft capsules, or of films, which are preferably orodispersible films, the step (b) is in particular performed by spreading the film-forming composition with low and constant thickness over a flat or cylindrical surface.

Preferably, the step (c) of drying is performed by heating at a temperature of less than 100° C., preferably of less than 80° C., preferably of between 30 and 50° C., for instance of between 35 and 45° C.

The film-forming compositions of the invention are thus really simple to carry out. Like for gelatin, solubilizing the ingredients, heating at moderate temperatures, and drying is sufficient to obtain the desired product.

The film-forming compositions of the invention might also be used for coating various products, like for instance meat, fourth range vegetables, pastries, confectioneries, flavorings, colors, polyunsaturated fatty acids, tablets, pellets.

The invention thus also covers coated products, the coating layer of which comprises:
a hydrolyzed alkylated starch;
an additional hydrocolloid;
isosorbide;
a plasticizer.

Preferably, the composition of the dry matter of the coating layer is like described before, for the film-forming composition according to the invention.

Preferably, the coating layer of those products is soluble in water a temperature chosen from 4 to 50° C., even from 20 to 40° C., for instance at room temperature (chosen from 20 to 25° C.), or at 37.5° C.

Preferably, the coating layer of those products is edible.

These products can be coated more precisely according to a method comprising the steps of:
(a) providing a film-forming composition according to the invention in the liquid form;
(b) coating a product with the composition obtained in step (a);
(c) drying the coated product obtained in step (b);
(d) recovering the coated product thus obtained.

This coating of step (b) can be for instance performed by dipping the product in the liquid film-forming composition, or by spraying the liquid film-forming composition onto and around the product to be coated.

The film-forming compositions of the invention might also be used for the manufacture of gastric gels, or of compositions for plaster sprays or of jelly confectionaries like for instance hard gums, soft gums, chewing pastes, licorices, jellies, pastilles, fruit pastes, caramels, toffees, fudges and fillings, and inclusions for ice creams or cakes.

Finally, the instant invention also covers the use of isosorbide for partial, or preferably total, replacement of gelatin in a film-forming composition comprising a hydrolyzed alkylated starch, or in a product comprising such film-forming composition or in a product obtainable from such film-forming composition.

Preferably, the film-forming composition is like described before.

Preferably, the product is like described before.

Unless otherwise specified, it should be understood in the instant invention that the expression "between X and Y" excludes the recited limits.

The following Examples serve to illustrate the invention and should by no means be construed so as to limit the scope of the invention.

EXAMPLES

In the following Examples, for convenient reading, the tests according to the invention are identified with the reference "IN-X", whereas the comparative tests are identified with the reference "CP-X".

1. Material

In the following tests, the following materials were used:

|  | Solid content |
|---|---|
| Starch: | |
| hydrolyzed hydroxypropylated pea starch (LYCOAT ® RS 780, Roquette Frères; having hydroxypropyl content of 7%; weight average molecular weight of 330 kDa; the pea starch from which it is derived having an amylose content of 35%) | 90.4% |
| Other hydrocolloids: | |
| κ-carrageenan | 87.0% |
| sodium alginate | 85.9% |
| Pluronic | ND |
| PVP | ND |
| Konjac | ND |
| Isosorbide | 99.8% |
| Plasticizer: | |
| Sorbitol | 99.4% |
| KCl | 99.9% |

2. Preparation of Film-Forming Compositions

In the following tests, film-forming compositions were prepared as follow.

The ingredients were weighed and dryly mixed. The premixed dry ingredients were added to hot deionized water under stirring (400 rpm). The mixture was heated at 90° C. for 1 hour using water bath for solubilizing all ingredients. The hot mixture was then kept at 70° C. overnight (about 15 hours) in order to eliminate the bubbles.

3. Preparation of Hard Capsule Shells

The clear homogenous solution obtained according to point 2. above was transferred to a container (for dipping) and kept at 70° C. The pins were oiled and molding was performed by dipping. After dipping the pins were turned several times in order to ensure homogenous thickness of the molded composition surface. The molded pins were dried in the oven at 40° C. for about one hour and collected. Hard capsule shells were assembled so as to form (empty) capsules and stored in humidity and temperature controlled area plastic bottle.

4. Preparation of Soft Capsule Shells

The clear homogenous solution obtained according to point 2. above was spread on a flat surface, so as to obtain a film having the thickness classically required to prepare soft capsule shells.

Example 1

Evaluation of Film-Forming Compositions not Containing Isosorbide, for the Preparation of Hard Capsule Shells This Example only describes film-forming compositions not complying with the invention. In this example, the inventors tried to obtain the best hard capsule shells they could, without using isosorbide.

7 series of tests were performed, which are summarized in the following table:

|  | hydrolyzed alkylated Starch | Additional hydrocolloid | | Sorbitol | KCl | Pluronic | Water |
|---|---|---|---|---|---|---|---|
| CP-1 | 25-30 g | 0.2-0.5 g | K-carrageenan | 5-10 g | 50-100 mg | — | 60 g |
| CP-2 | 28 g | 0.3 g | K-carrageenan | 15 g | 50 mg | — | 60 g |
| CP-3 | 25-30 g | 0.2-0.5 g | K-carrageenan | 5-10 g | 50-100 mg | — | 60 g |
|  |  | 0.5-2 g | PVP |  |  |  |  |
| CP-4 | 25-30 g | 0.2-0.5 g | K-carrageenan | 5-10 g | 50-100 mg | 1 g | 60 g |
| CP-5 | 25-30 g | 0.2-0.5 g | K-carrageenan | 5-10 g | 50-100 mg | 1 g | 60 g |
|  |  | 1 g | PVP |  |  |  |  |
| CP-6 | 27 g | 0.5 g | K-carrageenan | 8 g | 50 mg | — | 60 g |
|  |  | 0.5-2 g | Sodium alginate |  |  |  |  |
| CP-7 | 25 g | 0.5 g | K-carrageenan | 8 g | 50 mg | — | 63 g |
|  |  | 2 g | Konjac glue. |  |  |  |  |

Note:

in this table, weights of ingredients are not in dry weights. They thus include the intrinsic water of the powdery ingredients.

Test CP-1 and CP-2:

It was first tried to vary the content of hydrolyzed alkylated starch, κ-carrageenan, sorbitol and KCl in film-forming compositions. Hard capsule shells were obtained by using the following formula: 28 g hydrolyzed alkylated starch, 0.3 g K-carrageenan, 8 g sorbitol, 50 mg KCl. The hard capsules obtained thereof had good transparency and satisfying physical properties. However, they were not stable. Only after 2-days exposure at room temperature, the capsules became very brittle.

It was then tried to increase the amounts of plasticizer (test CP-2). However, after one hour drying, the capsules were still too soft. Moreover, they were still very unstable. After being kept 1 month in a well-sealed bottle, the hard capsules lost their transparency and became white.

As a conclusion, among all the amounts of hydrolyzed alkylated starch, κ-carrageenan, sorbitol and KCl, no ideal formula could be found. The capsules always lacked stability.

Test CP-3 to CP-5:

Polyvinyl porrolidone (PVP) was added to the formula. Different amounts were tested (test CP-3). However, the formed hard capsules were too soft and not very sable (no more than one month).

A surface active agent Pluronic was added to the formula (test CP-4). The stability of the formed hard capsules was slightly improved, but the hard capsules lost their transparency.

Both Pluronic and PVP were then added to the basic formula (test CP-5), but no significant improvement has was observed. Moreover, both PVP and Pluronic have the disadvantage of being petroleum-based products.

Test CP-6:

Sodium alginate was then added. Different amounts were tested. Stability of the hard capsules was improved significantly, but was still insufficient: after 2 months, the hard capsules started to lose their transparency and to become white.

Test CP-7:

It was also tried to use Konjac glucomannan. However the prepared solutions for dipping were not homogeneous. The phase separation was observed in the resulted hard capsules shells, and their transparency decreased.

Example 2

Evaluation of Film-Forming Compositions Containing Isosorbide, for the Preparation of Hard Capsule Shells 2.1. Film-Forming Composition Having Variable Ratio of Plasticizer to Isosorbide, and Variable Ratio of Isosorbide and Plasticizer to Hydrolyzed Alkylated Starch This Example describes film-forming compositions according to the invention as well as film-forming compositions not complying with the invention. In this example, the inventors varied the dry weight ratio of plasticizer (sorbitol) to isosorbide, and the dry weight ratio of isosorbide and plasticizer (sorbitol) to hydrolyzed alkylated starch.

8 tests were performed, which are summarized in the following table:

|  | Isosorbide | Sorbitol | Ratio of sorbitol to isosorbide (dry weight) | Ratio of isosorbide and sorbitol to hydrolyzed alkylated starch (dry weight) | |
|---|---|---|---|---|---|
| IN-1 | 4.00 g | 1.00 g | 0.25 | 0.20 | 27 g hydrolyzed |
| IN-2 | 5.50 g | 0.38 g | 0.07 | 0.24 | alkylated starch |
| IN-3 | 3.38 g | 2.50 g | 0.74 | 0.24 | 0.5 g κ-carrageenan |
| IN-4 | 2.50 g | 3.37 g | 1.34 | 0.24 | 1.5 g Sodium alginate |
| IN-5 | 7.00 g | 1.00 g | 0.14 | 0.33 | 50 mg KCl |
| IN-6 | 5.50 g | 2.50 g | 0.45 | 0.33 | 60 g water |
| IN-7 | 4.00 g | 4.00 g | 1.00 | 0.33 |  |
| CP-8 | 5-15 g | — | — | 0.20-0.61 |  |

Note:

in this table, weights of ingredients are not in dry weights. They thus include the intrinsic water of the powdery ingredients. However, the ratios are well expressed in dry weight.

Hard capsules obtained with film-forming compositions IN-1 to IN-7 according to the invention had very good transparency. Even after 3-months exposure at room temperature, hard capsules did not become white.

Moreover the capsule shells exhibited very good mechanical resistance, solubility, flexibility, drought resistance, moisture proof and disintegration.

Film-forming compositions IN-2 to IN-4 in particular, which exhibit a dry weight ratio of isosorbide and plasticizer to hydrolyzed alkylated starch of between 0.20 and 0.30, showed particularly good film-forming properties, and the resulted hard capsule shells were very stable.

For comparative tests CP-8, it was tried to form hard capsule shells by using various amounts of isosorbide, but without using plasticizers. No hard capsule shells could be formed. A thin solid was found on the pins, which was impossible to unmold.

2.2. Film-Forming Composition According to the Invention Comprising Gellan Gum as the Gelling Agent The inventors replaced the mixture of K-carrageenan and of sodium alginate by gellan gum in the compositions of Example 2.1. Excellent results were also obtained.

2.3. Comparative Film-Forming Composition Using a Starch not Complying with the Invention The inventors also tried to use various starches so as to prepare hard capsules, but failed in solving the problem of the invention. The starches used were the followings:

|  | Modifications | Amylose content of the starch from which it is dervied |
|---|---|---|
| Maize starch | hydroxypropylated | <1% |
| Pregelatinized potato starch | — | 23% |
| Maize starch | Hydrolyzed (Mw 400 kDa) | 25% |
| Maize starch | Hydrolyzed (Mw 100 kDa) | 25% |
| Maize starch | Hydrolyzed (Mw 15 kDa) | 25% |
| Maize starch | Hydrolyzed (Mw 9 kDa) | 25% |
| Maize starch | Hydrolyzed (Mw 7 kDa) | 25% |
| Maize starch | Hydrolyzed (Mw 2 kDa) | 25% |

The inventors tried numerous film-forming compositions with those starches including mixtures thereof so as to adjust viscosity of the film-forming composition.

The results can be summarized as follow:
the film-forming compositions were not suitable for use in the industrial equipment classically used for the manufacture of gelatin-based capsules (bad gelling properties, and/or bad rheological behavior), that is to say that these composition would have had required equipment changes for manufacturers of capsules in order to be properly handled; or
the capsules obtained exhibited poor properties, in particular in terms of transparency.

Example 3

Evaluation of Film-Forming Compositions Containing Isosorbide, for the Preparation of Soft Capsule Shells This Example describes a film-forming composition according to the invention, suitable for the preparation of soft capsule shells. In this Example, a film-forming composition having the following formula was prepared:

|  | Isosorbide | Sorbitol | Ratio of sorbitol to isosorbide (dry weight) | Ratio of isosorbide and sorbitol to hydrolyzed alkylated starch (dry weight) | |
|---|---|---|---|---|---|
| IN-8 | 2.5 g | 7.62 g | 3.04 | 0.41 | 27 g hydrolyzed alkylated starch 0.5 g κ-carrageenan 1.5 g Sodium alginate 50 mg KCl 60 g water |

Note:
in this table, weights of ingredients are not in dry weights. They thus include the intrinsic water of the powdery ingredients. However, the ratios are well expressed in dry weight.

Films obtained with film-forming compositions IN-8 had very good transparency, stability, mechanical resistance, solubility, flexibility, drought resistance, moisture proof and disintegration.

The film-forming compositions of the invention are thus suitable for the preparation of films and of soft capsules.

The invention claimed is:

1. A film-forming composition in liquid aqueous form comprising:
a hydrolyzed alkylated starch;
an additional hydrocolloid;
isosorbide; and
a plasticizer,
wherein the dry matter content by weight is between 10% and 70%.

2. The film-forming composition of claim 1, wherein the plasticizer is selected from sorbitol, glycerol, trehalose, triethyl citrate, polysorbate, Carnauba wax, hydrogenated castor oil, and mixtures thereof.

3. The film-forming composition of claim 2, wherein the plasticizer is selected from glycerol, trehalose, sorbitol, and mixtures thereof.

4. The film-forming composition according to claim 1, wherein the plasticizer at least comprises sorbitol, and optionally glycerol.

5. The film-forming composition according to claim 1, wherein the hydrolyzed alkylated starch is a hydrolyzed hydroxypropylated starch.

6. The film-forming composition according to claim 1, wherein said hydrolyzed alkylated starch is derived from a starch exhibiting an amylose content within a range of from 25 to 45%; these percentages being expressed in dry weight of amylose with respect to the total dry weight of said starch from which it is derived.

7. A product comprising the film-forming composition of claim 1.

8. The product of claim 7, which is edible.

9. The product according to claim 7, which is a capsule shell, a capsule, a film, a coated product, a jelly confectionary, a plaster spray composition, and a gastric gel.

10. A method for the manufacture of an article, comprising forming a film or a gel from a film-forming composition according to claim 1, and forming as an article one of a capsule shell, a capsule, a coated product, a jelly confectionary, a plaster spray, and a gastric gel.

11. The film-forming composition of claim 1, wherein the dry weight ratio of the sum of isosorbide and plasticizer to hydrolyzed alkylated starch is between 0.05:1 and 0.80:1.

12. The film-forming composition of claim 1, wherein the hydrocolloid is selected from gelatin, hydroxypropylmethylcellulose, hydroxypropylcellulose, polyvinyl alcohol, and mixtures thereof.

13. The film-forming composition of claim 1, wherein a dry weight ratio of the hydrocolloid to hydrolyzed alkylated starch is of between 0.01:1 and 0.50:1.

14. A film-forming composition in liquid aqueous form wherein the dry matter content by weight of the composition is between 10% and 70%, the composition comprising a hydrolyzed alkylated starch and an additional hydrocolloid with a dry weight ratio of the hydrocolloid to hydrolyzed alkylated starch of between 0.01:1 and 0.50:1, isosorbide and a plasticizer comprising at least sorbitol with a dry weight ratio of the sum of isosorbide and plasticizer to hydrolyzed alkylated starch of between 0.05:1 and 0.80:1.

* * * * *